United States Patent [19]

Mizoguchi

[11] Patent Number: 5,792,619
[45] Date of Patent: Aug. 11, 1998

[54] ASSAY USING OXIDATIVE CHROMOGENIC REAGENT

[75] Inventor: Makoto Mizoguchi, Kumamoto, Japan

[73] Assignee: Dojindo Molecular Technologies, Inc., Bethesda, Md.

[21] Appl. No.: 792,828

[22] Filed: Jan. 30, 1997

[30] Foreign Application Priority Data

Dec. 16, 1996 [JP] Japan ........................... 8-335408

[51] Int. Cl.$^6$ ........................... G01N 33/52; C07C 309/14
[52] U.S. Cl. ........................... 435/7.91; 562/30
[58] Field of Search ........................... 560/150; 435/7.91; 562/30

[56] References Cited

FOREIGN PATENT DOCUMENTS 57-27106   6/1982   Japan .
58-9094    2/1983   Japan .

OTHER PUBLICATIONS

Trinder, P., Ann. Clin. Biochem., 6, 24–27, 1969.
Barham, D. Et al., Analyst (London) 97, 142–145, 1972.
Tamaoku, K., Murao, Y., et al., The Pharmaceutical Society of Japan, the 101st Annual Conference Abstracts, p. 148, 1981.
Tamaoku, K., Hirasaki, K. Et al., The Pharmaceutical Society of Japan, the 101st Annual Conference Abstracts, p. 148, 1981.
Tamaoku, K. Et al., Anal. Chim. Acta, 136, 121–127, 1982.
Tamaoku, K. Et al., Chem. Pharm. Bull., 30, 2492–2497, 1982.
Johnson, K.S. et al., Anal. Chim. Acta, 201, 83–84, 1987.
Madsen, B.C. et al., Anal. Chem. 56, 2849–2850, 1984.
Matsumoto, K., et al., Clinical Chemistry, 8, 63–72, 1979.
Morishita, Y. et al., Clinical Chemistry, 11, 88–97, 1982.
McGowan, M. et al., Microchem. J., 27, 564–573, 1982.
Fossati, P. et al., Clin. Chem., 26, 227–231, 1980.
Chemical Abstracts, vol. 112, 1990, Abstract No. 112(21) 194925e.
Mizoguchi et al., Bunseki Kagaku, vol. 45, No. 2., pp. 111–124, 1996.

Primary Examiner—Gary L. Kunz
Attorney, Agent, or Firm—Greenblum & Bernstein, P.L.C.

[57] ABSTRACT

An oxidative chromogenic reagent free from interference by bilirubin used for the measurement of a biogenic substance by an enzymatic analysis, which comprises a compound or a salt thereof represented by the following formula wherein $R^1$ and $R^2$ independently represent a $C_{3-4}$-alkly group substituted with a sulfonic acid group or a $C_{3-4}$-hydroxyalkyl group substituted with a sulfonic acid group; and $R^3$ and $R^4$ independently represent a $C_{1-4}$-alkyl group, a $C_{1-4}$-alkoxy group, a substituted or non-substituted carbamoyl group, an acyl-substituted amino group, an aryl group, or a halogen atom. The reagent is stable and has excellent water solubility, and it enables high sensitive and accurate measurement because interference by bilirubin is substantially reduced or eliminated.

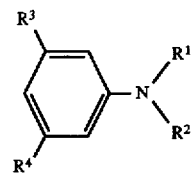

18 Claims, No Drawings

1

ASSAY USING OXIDATIVE CHROMOGENIC REAGENT

TECHNICAL FIELD

The present invention relates to an oxidative chromogenic reagent used for enzymatic analysis of biogenic substances such as glucose and cholesterol.

PRIOR ART

Enzymatic analyses have so far been developed as measuring methods of various biogenic substances contained in body fluids such as blood or urine, and the analyses have become widely used in ordinary clinical diagnosis. For example, glucose oxidase, cholesterol oxidase, and uricase are used for the measurement of glucose, cholesterol, and uric acid, respectively. The amount of each of the biogenic substances can be accurately measured by enzymatically and specifically decomposing the biogenic substances as substrates, and then quantifying the resulting generated hydrogen peroxide by means of, for example, chromogenic reaction.

In particular, since the Trinder method was proposed (Trinder, P., Ann. Clin. Biochem., 6, 24, 1969; Barham, D. and Trinder, P., Analyst (London), 97, 142, 1972), which comprises the steps of oxidatively coupling phenol as an oxidative chromogenic reagent with 4-aminoantipyrine as a coupling reagent by using an enzyme system comprised of glucose oxidase and peroxidase, and then followed by measuring the absorbance of a resulting dye to quantify hydrogen peroxide, methods of enzymatic measurement using oxidative chromogenic reagents have remarkably been developed. The enzymatic measurements are characterized by features of higher substrate specificity compared to measurement processes by means of chemical reactions, and excellent measurement accuracy. In addition, there is also an advantage that automatic processes are facilitated since reactions are completed under mild conditions. Therefore, they are expected to be become more widespread in the near future.

As oxidative chromogenic reagents used for the aforementioned enzymatic measurements, aniline derivatives have become used instead of the earlier used phenol that was used. Furthermore, several oxidative chromogenic reagents having improved water solubilities and wavelength properties have been reported (see, for example, Tamaoku, K., Murao, Y., et al., The Pharmaceutical Society of Japan, the 101st Annual Conference Abstracts, p.148, 1981; Tamaoku, K., Hirasaki, K., et al., the Pharmaceutical Society of Japan, the 101st Annual Conference Abstracts, p.148, 1981; Tamaoku, K., et al., Anal. Chim. Acta, 136, 121, 1982; Tamaoku, K., et al., Chem. Pharm. Bull., 30, 2492, 1982; Johnson, K. S., et al., Anal. Chim. Acta, 201, 83, 1987; Madsen, B. C., et al., Anal. Chem., 56, 2849, 1984).

As oxidative chromogenic reagents, each of the N-sulfoalkylaniline derivatives disclosed in Japanese Patent Publication (KOKOKU) No. (Sho) 57-27106/1982 and the N-hydroxysulfoalkylaniline derivatives disclosed in Japanese Patent Publication (KOKOKU) No. (Sho) 58-9094/1983 has been developed and put to practical use. These oxidative chromogenic reagents are characterized in that they react with 4-aminoantipyrine extremely rapidly and quantitatively in the presence of hydrogen peroxide and a peroxidase to form dyes having excellent color stability. The compounds have characteristic properties of excellent stability in an aqueous solution as well as high water-solubility. Accordingly, they have been widely and ordinarily used as standard chromogenic regents for enzymatic assays.

However, the reaction of dye formation by using these oxidative chromogenic reagents are susceptible to interferences caused by various reducing materials such as ascorbic acid and bilirubin that are contained in biological specimens, which may sometimes affect quantitative performances of the reactions. As for ascorbic acid, a method was proposed for preventing the interference in which ascorbate oxidase is added to decompose ascorbic acid. However, as for bilirubin, any effective means for preventing the interference has not yet been available to date. Generally used methods to eliminate the influence by bilirubin include some modifications of formulations of reagents used (Matsumoto, K., et al., Clinical Chemistry, 8, 63, 1979; Morishita, Y., et al., Clinical Chemistry, 11, 88, 1982).

As methods to achieve more active elimination of the interference by bilirubin, some methods have been proposed which include, for example, a method comprising the steps of reacting a known hydrogen donor with 4-aminoantipyrine in a system containing bilirubin, and choosing a combination exhibiting minimum interference; a method comprising the step of adding an excessive amount of 4-aminoantipyrine, a method comprising the step of adding potassium ferrocyanide that exhibits an oxidizing activity to bilirubin. However, any of these methods cannot completely eliminate the influence of bilirubin (McGowan, M., et al., Murochem. J., 27, 564, 1982; Fossati, P., et al., Clin. Chem., 26, 227, 1980).

DESCRIPTION OF THE INVENTION

An object of the present invention is to provide an oxidative chromogenic reagent used for enzymatic analysis of biogenic substances. More specifically, the object is to provide an oxidative chromogenic reagent with reduced or eliminated interference by bilirubin.

Another object of the present invention is to provide an oxidative chromogenic reagent having the aforementioned characteristics, wherein the agent has excellent water solubility and is stable in the state of an aqueous solution.

A further object of the present invention is to provide a highly sensitive oxidative chromogenic reagent which reacts with 4-aminoantipyrine rapidly and quantitatively and produces a coloring compound that can maintain excellent coloring stability for a long period of time.

The inventors of the present invention conducted various studies to achieve the foregoing objects, and as a result, they found that, by using the compound represented by the formula set out below as an oxidative chromogenic reagent for the enzymatic analysis, the interference by bilirubin can be reduced or eliminated, and accordingly, extremely sensitive and accurate quantitative analysis can be performed. The present invention was achieved on the basis of these findings.

The present invention thus provides an oxidative chromogenic reagent free from interference by bilirubin used for the measurement of a biogenic substance by an enzymatic analysis, which comprises a compound or a salt thereof represented by the following formula:

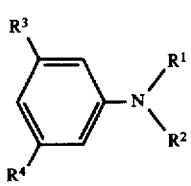

wherein $R^1$ and $R^2$ independently represent a $C_{3-4}$-alkyl group substituted with a sulfonic acid group or a $C_{3-4}$-hydroxyalkyl group substituted with a sulfonic acid group; and $R^3$ and $R^4$ independently represent a $C_{1-4}$-alkyl group, a $C_{1-4}$-alkoxy group, a substituted or non-substituted carbamoyl group, an acyl-substituted amino group, an aryl group, or a halogen atom.

According to preferred embodiments of the present invention, there are provided the aforementioned reagent which comprises the compound in the form of a sodium salt; the aforementioned reagent which comprises the compound or the sodium salt thereof wherein $R^1$ and $R^2$ are 4-sulfobutyl groups; and $R^3$ and $R^4$ are the same functional groups selected from the group consisting of a $C_{1-4}$-alkyl group and a $C_{1-4}$-alkoxy group; and the aforementioned reagent which comprises the compound or the sodium salt thereof wherein $R^1$ and $R^2$ are sulfobutyl groups; and $R^3$ and $R^4$ are methyl groups or $R^3$ and $R^4$ are methoxy groups. There is also provided a method for the measurement of a biogenic substance by an enzymatic analysis, characterized in that the aforementioned compound or a salt thereof is used as an oxidative chromogenic reagent so as to carry out the measurement free from interference by bilirubin. In addition, there is also provided, as one of embodiments of the present invention, a use of the aforementioned compound or a salt thereof as an oxidative chromogenic reagent free from interference by bilirubin for the measurement of a biogenic substance by an enzymatic analysis.

BEST MODE FOR CARRYING OUT THE INVENTION

The reagent of the present invention is an oxidative chromogenic reagent used for the enzymatic analysis, and it comprises a compound represented by the above general formula or a salt thereof. The reagent of the present invention is characterized in that the interference by bilirubin is substantially reduced or eliminated, and that accuracy and sensitivity of measurement is not substantially affected by bilirubin contained in a biogenic specimen, and accordingly, a biogenic substance can be accurately quantified.

In the above general formula, as for the $C_{3-4}$-alkyl group substituted by a sulfonic acid group and the $C_{3-4}$-hydroxyalkyl group substituted by a sulfonic acid group represented by $R^1$ and $R^2$, either of those having straight-chains or branched-chains may be used, and substituting position of a sulfonic acid group, or that of a hydroxyl group of the hydroxyalkyl group are not particularly limited. For example, n-propyl group and hydroxy-n-propyl group substituted with a sulfonic acid group at their ends, or n-butyl group and hydroxy-n-butyl group substituted with a sulfonic acid group at their ends are preferred. More preferably, n-butyl group and hydroxy-n-butyl group substituted with a sulfonic acid group at their ends, and most preferably, n-butyl group substituted with a sulfonic acid group at its end may be used. Although $R^1$ and $R^2$ may be the same or different, it is preferred that both are n-butyl groups substituted with sulfonic acid groups at their ends (4-sulfo-1-butyl group).

The $C_{1-4}$-alkyl group and the $C_{1-4}$-alkoxy group represented by $R^3$ and $R^4$ may be either of those having straight-chains or branched chains. As the $C_{1-4}$-alkyl group, for example, methyl group, ethyl group, n-propyl group, iso-propyl and the like are preferred, and as the $C_{1-4}$ alkoxy group, for example, methoxy group, ethoxy group, n-propoxy group, isopropoxy group and the like are preferred. As the substituted carbamoyl group represented by $R^3$ and $R^4$, those having one or two $C_{1-4}$-alkyl groups on the amino group may be used. As the acyl group that substitutes on the amino group of the acyl-substituted amino group, a $C_{1-4}$-alkylcarbonyl group such as acetyl group, a halogenated $C_{1-4}$-alkylcarbonyl group such as trifluoroacetyl group, or an arylcarbonyl group such as benzoyl group may be used. As the aryl group represented by $R^3$ and $R^4$, phenyl group, naphthyl group or the like may be used. As the halogen atom represented by $R^3$ and $R^4$, any one of fluorine atom, chlorine atom, bromine atom, or iodine atom may be used. Although $R^3$ and $R^4$ may be the same or different, they are preferably the same. For example, compounds wherein both of $R^3$ and $R^4$ are methyl groups, or both of $R^3$ and $R^4$ are methoxy groups are preferably used.

As the salt of the compound represented by the above formula, for example, a metal salt such as sodium salt, potassium salt, and calcium salt; as well as an ammonium salt, triethylamine salt or the like may be used. Among the compounds mentioned above, known compounds can be prepared according to methods described in the literature (for example, CA:112(21)194925e discloses 3,5-dimethyl-N,N-di-(3-sulfo-1-propyl)aniline) and other compounds can also be easily manufactured according to preparation processes that are known, per se, (see, the aforementioned literature and the patent publications about oxidative chromogenic reagents).

Examples of the compounds most preferably used for the reagent of the present invention are described below. However, the scope of the present invention is not limited to the following compounds.

Compound A: $R^1=R^2=CH_2CH_2CH_2CH_2SO_3Na$, $R^3=R^4=CH_3$

Compound B: $R^1=R^2=CH_2CH_2CH_2SO3Na$, $R^8=R^4=CH_3$

Compound C: $R^1=R^2=CH_2CH_2CH_2CH_2SO_3Na$, $R^3=R^4=OCH_3$

Compound D: $R^1=R^2=CH_2CH_2CH_2SO_3Na$, $R^3=R^4=OCH_3$

The reagent of the present invention comprises one or more, preferably one of the aforementioned compounds, and if desired, may further contain other ingredients required for oxidative coloring reactions and additives for formulations or the like. Examples of these components include buffering agents, detergents, pH modifiers, solubilizers, binders, excipients, coating agents and the like. The reagents of the present invention may preferably be provided as tablets, lyophilized preparations and the like that can be prepared by conventional methods, and they are preferably used by being dissolved before use in a suitable aqueous solvent such as distilled water, distilled water for injection, or buffered solutions. Methods of their use as oxidative chromogenic reagents and reaction conditions may be in accordance with methods and conditions well-known and widely-used so far by those skilled in the art (see, for example, the above-cited literature concerning oxidative chromogenic reagents), and their examples are specifically described in Examples of the specification. Analytic objective substances for the reagent of the present invention are not particularly limited so long as they can be measured by enzymatic analyses. For example, the reagents may preferably be used for measurements of glucose, cholesterol, and uric acid.

EXAMPLES

Example 1
Preparation of Compound C($R^1=R^2=CH_2CH_2CH_2CH_2SO_3Na$, $R^3=R^4=OCH_3$)

A mixture of 3,5-dimethoxyaniline (25 g, 183.6 mmol), dimethylformamide (500 ml), and butane sultone (75 g, 550.8 mmol) was heated at 100° C. for 8 hours with stirring. The mixture was added with sodium carbonate (10.6 g), and then, stirring was continued for 8 hours under heating at 100° C. Progress of the reaction was checked by using thin layer chromatography (silica gel, chloroform:methanol=1:1, Rf=0.2) and the reaction was stopped when dibutylsulfonate occupied most of the product. The reaction mixture was concentrated under reduced pressure to obtain brown oil. The oil was dissolved in purified water (500 ml), and the resulting solution was neutralized and concentrated under reduced pressure. The residue was added with ethanol (700 ml) and crystallized with warming, and the resulting crystals were recrystallized from ethanol to obtain white crystals of the title compound (24 g, 51.1 mmol).

$^1$H-NMR ($D_2O$), δppm (TMS):1.43(m, 8H), 2.03(s, 6H), 2.70(t, 4H), 3.06(t, 4H), 6.31(s,; 1H), 6.35(s, 2H); IR ($cm^{-1}$) 3480, 1595, 1235, 1110

Example 2
Test Example

The following reagent solutions were prepared.
Reagent solution 1:

Each of Compounds A to D, phenol, or N,N-dimethylaniline was dissolved in 50 mM phosphate buffer (pH 7.0) at 10 mM. Compounds A to D became dissolved immediately and gave uniform solutions, and no precipitation of crystals was observed even after storage. In a similar manner, 10 mM solutions of an N-sulfoalkyl-aniline derivative described in the Japanese Patent Publication (KOKOKU) No. (Sho) 57-27106/1982 (Compound "M" shown in Table 1 of the publication) and an N-hydroxysulfoalkylaniline derivative described in the Japanese Patent Publication (KOKOKU) No. (Sho) 58-9094/1983 (Compound "L" shown in Table 1 of the publication) were prepared.

Reagent solution 2:

4-Aminoantipyrine was dissolved in 50 mM phosphate buffer (pH 7.0) at 10 mM.

Reagent solution 3:

Hydrogen peroxide was dissolved in purified water at 2 mM.

Reagent solution 4:

Peroxidase (Wako Pure Chemical Industries, Ltd.) was dissolved in 50 mM phosphate buffer (pH 7.0) at 330 U/ml.

Each 30 μl of Reagent solution 1, Reagent solution 2, and Reagent solution 4 was added to 3 ml of 50 mM phosphate buffer (pH 7.0), and then the mixture was incubated at 37° C. for 10 minutes. The reaction mixture was added with Reagent solution 3 (30 μl), and incubation was further continued at 37° C. for 5 minutes. Then, absorption spectrums of the reaction mixtures were measured. The results are shown in Table 1. From these results, it is apparent that Compounds A to D have sensitivities and detection wavelengths comparable to conventional oxidative chromogenic reagents. In addition, as for the reagents of the present invention (Compounds A to D), no substantial change of absorbance was observed at least for hours, and accordingly, they were verified to have excellent coloring stabilities.

TABLE 1

| Compound | Maximum Absorption wavelength (nm) | Absorbance |
|---|---|---|
| Compound A | 625 | 0.260 |
| Compound B | 552 | 0.454 |
| Compound C | 592 | 0.201 |
| Compound D | 590 | 0.221 |
| Phenol | 505 | 0.116 |
| N,N-dimethylaniline | 560 | 0.422 |
| Compound M* | 561 | 0.317 |
| Compound L$^b$ | 555 | 0.443 |

*N-sulfoalkylaniline derivative described in Table 1 of the Japanese Patent Publication (KOKOKU) No. (Sho) 57-27106/1982
$^b$N-hydroxysulfoalkylaniline derivative mentioned in the Japanese Patent Publication (KOKOKU) No. (Sho) 58-9094/1983

Example 3
Test for interference by bilirubin

Reagent Solutions 1 to 4 were prepared as in Example 2. As a bilirubin solution, a solution of conjugate type bilirubin (220 mg/dl, Kokusai Shiyaku Co., Ltd., Interference Check: A Plus) was used. Each 30 μl of Reagent solution 1, Reagent solution 2, and Reagent solution 4 was added to 3 ml of 50 mM phosphate buffer (pH 7.0) and then the mixture was incubated at 37° C. for 10 minutes. The reaction mixture was added with 5 μl of the bilirubin solution and incubated at 37° C. for 1 minute. Then, the mixture was added with 30 μl of Reagent solution 3 and incubated at 37° C. for 5 minutes, and absorption spectrum of the reaction mixture was measured. Measurements of the absorbance were carried out at maximum absorption wavelengths of the respective reagents used. The results were compared with those of Example 2, and reductions of sensitivity in the presence of bilirubin were calculated by the following equation: Influence by bilirubin (%)=[Absorbance obtained in Example 3 (Abs-2) /Absorbance obtained in Example 2 (Abs-1)]×100. The results are shown in Table 2. From these results, it is apparent that the reagents of the present invention are not substantially interfered by bilirubin.

TABLE 2

| Compound | Measurement wavelength (nm) | Abs-1 | Abs-2 | Influence of bilirubin (%) |
|---|---|---|---|---|
| Compound A | 625 | 0.260 | 0.240 | 92.3 |
| Compound B | 552 | 0.454 | 0.428 | 94.3 |
| Compound C | 592 | 0.201 | 0.195 | 97.0 |
| Compound D | 590 | 0.221 | 0.212 | 95.9 |
| Phenol | 505 | 0.116 | 0.083 | 71.6 |
| N,N-dimethylaniline | 560 | 0.422 | 0.324 | 76.8 |
| Compound M* | 561 | 0.317 | 0.250 | 78.9 |
| Compound L$^b$ | 555 | 0.443 | 0.327 | 73.8 |

*N-sulfoalkylaniline derivative described in Table 1 of the Japanese Patent Publication (KOKOKU) No. (Sho) 57-27106/1982
$^b$N-hydroxysulfoalkylaniline derivative described in the Japanese Patent Publication (KOKOKU) No. (Sho) 58-9094/1983

Industrial Applicability

The reagent of the present invention have excellent water solubility and is stable in an aqueous solution for a long period of time. In addition, the reagent of the present invention has high sensitivity, and characterized in that interference by bilirubin is substantially reduced or eliminated.

What is claimed is:

1. A method for measurement of a biogenic substance, comprising enzymatically reacting the biogenic substance with a composition containing at least one enzyme and, as an oxidative chromogenic reagent, N,N-bis(4-sulfobutyl)-dimethoxyaniline or a salt thereof, which is not subject to interference by bilirubin, and evaluating results of the reaction.

2. The method according to claim 1, wherein the oxidative chromogenic composition comprises a sodium salt of N,N-bis(4-sulfobutyl)-dimethoxyaniline.

3. The method according to claim 1, wherein the oxidative chromogenic composition further comprises a coupling agent.

4. The method according to claim 3, wherein said coupling agent is 4-aminoantipyrine.

5. The method according to claim 2, wherein the oxidative chromogenic composition further comprises a coupling agent.

6. The method according to claim 5, wherein said coupling agent is 4-aminoantipyrine.

7. An oxidative chromogenic compound free from interference by bilirubin for measurement of a biogenic substance by enzymatic analysis, which compound is N,N-bis(4-sulfobutyl)-dimethoxyaniline or a salt thereof.

8. The compound according to claim 7, which is a sodium salt of N,N-bis(4-sulfobutyl)-dimethoxyaniline.

9. A composition comprising the oxidative chromogenic compound according to claim 7 and a coupling agent.

10. The composition according to claim 9, wherein said coupling agent is 4-aminoantipyrine.

11. A composition comprising the oxidative chromogenic compound according to claim 8 and a coupling agent.

12. The composition according to claim 11, wherein said coupling agent is 4-aminoantipyrine.

13. An oxidative chromogenic composition free from interference by bilirubin for measurement of a biogenic substance by enzymatic analysis, comprising at least one enzyme and N,N-bis(4-sulfobutyl)-dimethoxyaniline or a salt thereof.

14. The composition according to claim 13, wherein said N,N-bis(4-sulfobutyl)-dimethoxyaniline or a salt thereof is a sodium salt of N,N-bis(4-sulfobutyl)-dimethoxyaniline.

15. The composition according to claim 13, further comprising a coupling agent.

16. The composition according to claim 15, wherein said coupling agent comprises 4-aminoantipyrine.

17. The composition according to claim 14, further comprising a coupling agent.

18. The composition according to claim 17, wherein said coupling agent is 4-aminoantipyrine.

* * * * *